United States Patent [19]

Sarstedt et al.

[11] Patent Number: 5,801,062
[45] Date of Patent: Sep. 1, 1998

[54] METHOD AND DEVICE FOR PROVIDING AND SPREADING FLUIDS

[75] Inventors: Walter Sarstedt, Rommelsdorfer Strasse, 51582 Nuembrecht; Matthias Pfeiffer, Münsing/Ambach; E. Henkel, Hannover, all of Germany

[73] Assignee: Walter Sarstedt, Nuembrecht, Germany

[21] Appl. No.: 586,074

[22] Filed: Jan. 16, 1996

[30] Foreign Application Priority Data

Jan. 13, 1995 [DE] Germany .................. 195 00 915.0

[51] Int. Cl.⁶ .................................................. G01N 1/10
[52] U.S. Cl. .................. 436/180; 118/120; 118/401; 422/99; 422/100; 427/2.11; 435/309.1; 436/174; 604/411
[58] Field of Search ......................... 436/174, 180; 422/99, 100; 435/309.1; 604/411, 412, 413, 414; 427/2.11; 118/401, 415, 120

[56] References Cited

U.S. PATENT DOCUMENTS

| | | |
|---|---|---|
| 3,366,278 | 1/1968 | Forbes . |
| 3,880,111 | 4/1975 | Levine et al. . |
| 4,027,623 | 6/1977 | Adler . |
| 4,030,341 | 6/1977 | Sullivan . |
| 4,285,907 | 8/1981 | Hugemann et al. ............ 422/100 |
| 4,378,333 | 3/1983 | Laipply . |
| 4,563,104 | 1/1986 | Saint-Amand . |
| 5,114,862 | 5/1992 | Brenneman ............... 436/169 |
| 5,163,583 | 11/1992 | Whitworth . |
| 5,286,453 | 2/1994 | Pope . |
| 5,439,649 | 8/1995 | Tseung et al. .............. 422/99 |
| 5,494,828 | 2/1996 | Leopando ................ 436/180 |

FOREIGN PATENT DOCUMENTS

| | | |
|---|---|---|
| 2452267 | 5/1975 | Germany . |
| 2627416 | 1/1977 | Germany . |
| 2642777 | 3/1978 | Germany . |
| 9209084 | 10/1992 | Germany . |
| 9214227.3 | 4/1994 | Germany . |
| 1558138 | 9/1977 | United Kingdom . |

*Primary Examiner*—Jan Ludlow
*Attorney, Agent, or Firm*—Greenblum & Bernstein, P.L.C.

[57] ABSTRACT

For the removal of a small amount of fluid, in particular blood, from a sealed container, and the deposition of a drop of fluid on a slide by a dropper, and the subsequent spreading of the drop, the rear end of a dropper needle having a longitudinal channel which passes therethrough is pressed through a seal into a container. Once the needle is inserted into the container, a drop of fluid moves out of the container via the longitudinal channel to a slide. After depositing the drop of fluid on the slide, the dropper itself is used to spread and distribute the drop of fluid on the slide, so that spreading of the drop of fluid is facilitated and hazardous waste is reduced to a minimum. The dropper used for this purpose is made integral with a spreader.

19 Claims, 1 Drawing Sheet

# METHOD AND DEVICE FOR PROVIDING AND SPREADING FLUIDS

BACKGROUND OF THE INVENTION

The invention relates to the removal of fluids, in particular blood, in small amounts from closed containers, and the depositing of drops of fluid on a slide by means of a dropper, and the subsequent spreading of the drop.

To examine blood or other serum or fluid samples, e.g. cerebro-spinal fluid or pleurocentesis fluid, a drop of this sample is applied to a plate-like slide, and subsequently distributed or spread by drawing the spreader uniformly in the longitudinal direction of the slide, and then observed under the microscope.

U.S. Pat. Nos. 3,366,278, 5,163,583, and 5,286,453, disclose removing the fluid to be examined from the closed containers, in particular elongate tubes. For this purpose, a resilient stopper or a membrane closing the open end of the tube is pierced by a dropper needle which has a longitudinal channel passing therethrough and which enters the container in this way. A connection between the interior of the container and the environment therefore arises so that a drop of fluid can be removed and deposited on the slide.

The drop-like fluid applied can be spread or distributed uniformly by a second slide, namely a glass or plastic spreader, for example as known from DE-U 92 142 227.3, which has spreading edges and which may be polished in a particular way.

The compulsory use of a dropper and a spreader has the consequence that several objects always have to be discarded in a special manner after use, for particularly in blood and serum examinations the fact that these objects are contaminated by contact with potentially infectious samples cannot be ruled out. Consequently, these objects are included in hazardous waste, and the disposal thereof leads to high outlay and cost.

SUMMARY OF THE INVENTION

The object of the invention is therefore to produce a method and a device to facilitate spreading of the drop of fluid and to be able to reduce or minimize the amount of hazardous waste to be discarded.

This object is attained in an amazingly simple way in accordance with the invention in that the drop of liquid is spread and distributed on the slide with the dropper. As a result of the step of using the dropper itself as the spreader, the costly apparatus coming into contact with a possibly infectious fluid sample can be limited to one part so that the volume of rubbish to be discarded is reduced considerably, since a second slide or a separate spreader is not required.

To attain the object, it is also proposed to form the dropper integrally with spreader means. For this purpose, the front end of the dropper which is at a distance from the container can, for example, be provided with a radially projecting spreader attachment or cross member having the spreading edge required to distribute the drop of fluid on the slide. To distribute the drop of fluid, it is also possible to remove the dropper, before spreading, from the container (referred to as sample tube below) or to leave the dropper in its mounted position on the sample tube, depending on what is required and what in practice enables easier manipulation.

Accordingly, in one aspect the invention provides a method for the removal of fluids, in particular blood, in small amounts from closed containers, and the depositing thereof as drops of fluid on a slide by means of a dropper, and the subsequent spreading of the drop, wherein the rear end of a dropper needle having a longitudinal channel passing therethrough is pressed through a seal into the container, and a drop of fluid moves out of the container via the longitudinal channel to the slide, the drop of fluid being spread and distributed on the slide using the dropper.

In another aspect the invention provides a device for the removal of fluids, in particular blood, in small amounts from closed containers, and the depositing thereof as drops of fluid on a slide by means of a dropper, and the subsequent spreading of the drop, wherein the rear end of a dropper needle having a longitudinal channel passing therethrough is adapted to be pressed through a seal into the container, a drop of fluid moving out of the container via the longitudinal channel to the slide, wherein the dropper is provided with spreader means.

In a further aspect the invention provides a device for the removal of fluids, in particular blood, in small amounts from closed containers, and the depositing thereof as drops of fluid on a slide by means of a dropper, and the subsequent spreading of the drop, wherein the rear end of a dropper needle having a longitudinal channel passing therethrough can be pressed through a seal into the container, a drop of fluid moving out of the container via the longitudinal channel to the slide, wherein the a dropper is provided with spreader means and is carried by the container.

BRIEF DESCRIPTION OF THE DRAWINGS

Further details and advantages of the invention can be seen in the claims and the description below, in which an embodiment of the invention is explained in greater detail with reference to the accompanying drawings, in which:

DESCRIPTION OF THE PREFERRED EMBODIMENT

Figure 1:
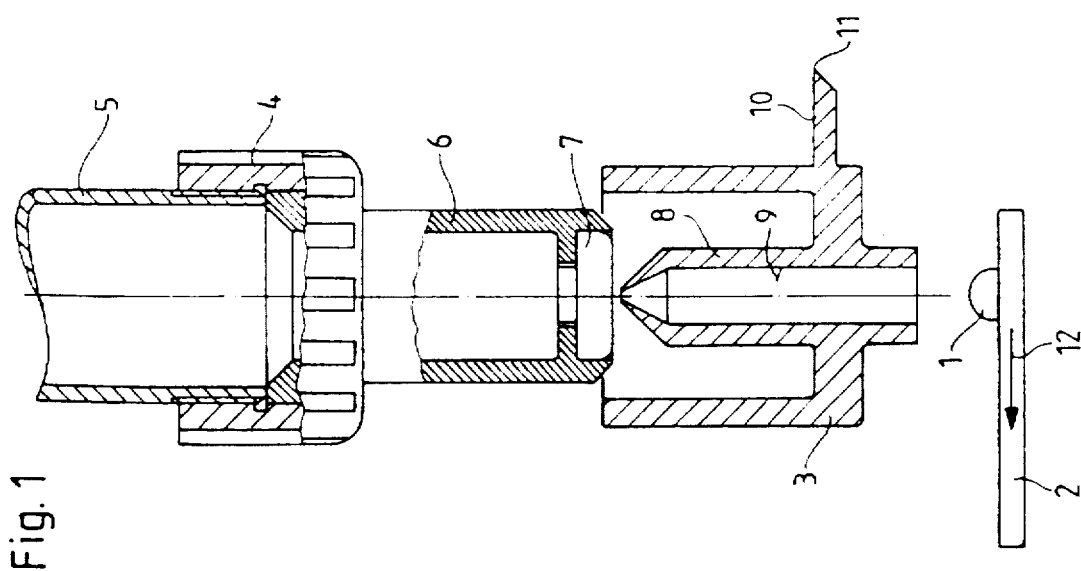
FIG. 1 is a partial longitudinal section of an exploded and simplified representation of a device for the removal of a drop of fluid from a sample tube and the application or deposition thereof on a slide.

To apply a drop of fluid 1 to a plate-like slide 2 (cf. also FIG. 2), a dropper 3 is attached as shown in FIG. 1 to the end, closed by a screw cap 4 of a closed sample tube 5 containing the fluid, in particular blood. The screw cap 4 has a cylindrical attachment 6 which extends the sample tube 5 and which receives a resilient closing stopper (membrane) 7 closing the interior of the tube 5.

As the dropper 3 is mounted on the cylindrical attachment 6 of the cap 4 screwed to the sample tube 5, the closing stopper 7 is pierced by a dropper needle 8, having a longitudinal channel 9 passing therethrough, so that the pointed rear end of the dropper needle 8 enters the sample tube 5 or the attachment 6 connected thereto; in this connection the resilient material of the closing stopper or membrane 7 forms a seal around the dropper needle 8. Consequently a fluid connection is produced between the inside of the sample tube 5 and the environment, and the drop of fluid 1 moves via the longitudinal channel 9 of the dropper needle 8 to the slide 2 (cf. FIG. 1).

The dropper 3 is provided integrally with spreader means 10 which, in the embodiment, is in the shape of a spreader cross member which projects radially at the front end of the dropper, at a distance from the dome or attachment 6 of the screw cap 4, and which protrudes beyond both sides of the dropper transversely to the longitudinal direction thereof; in this connection unity may also be obtained by the spreader means 10 being locked or otherwise fixed to the dropper 3, if it is not preferably already provided thereon when the dropper is being manufactured. The spreader means 10 has a linear spreading edge 11 ensuring fine distribution of the drop of fluid 1 on the slide 2. Thus, in addition to its function of removing the drop of liquid 1 and applying it to the slide 2, the dropper 2 also acts as a spreader.

Figure 2:
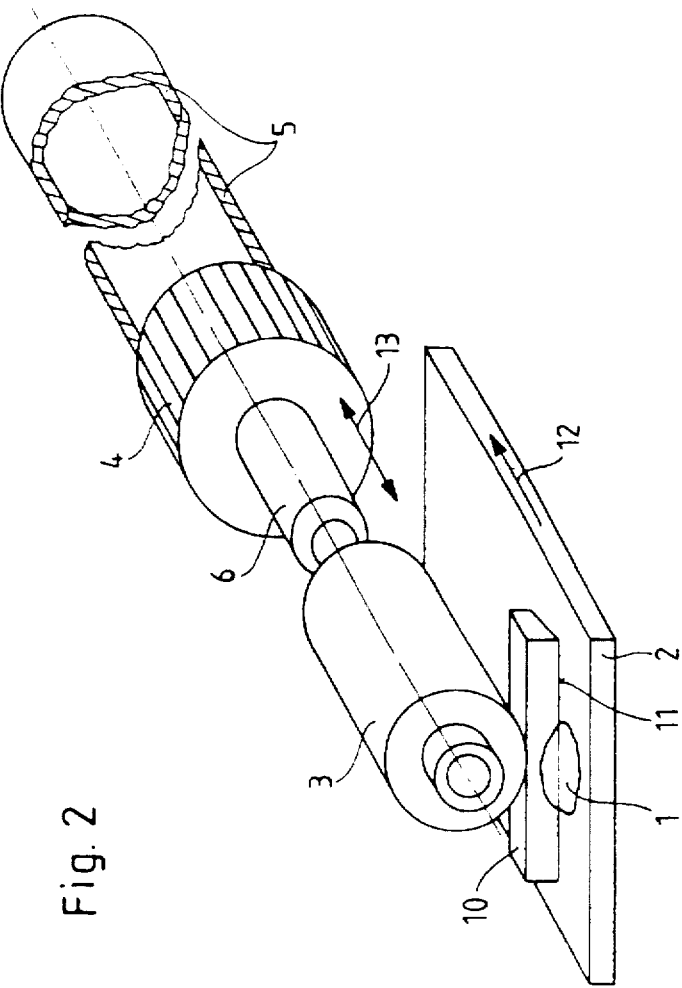
FIG. 2 is a simplified representation, in perspective view, of the device shown in FIG. 1, in a position for spreading and distributing the applied drop of liquid on the surface of the slide.

To spread the drop of fluid 1, the dropper 3 occupies, for example, the position shown in FIG. 2, in which it is moved in the direction of the arrow 12 substantially parallel to the slide 2, and the fluid is consequently distributed advantageously along the length of the slide 2 over a width corresponding to the dimension of the spreading edge 11 as it is drawn along the slide. This can, as shown in FIG. 2, occur with the sample tube 5 removed from the dropper 3, i.e. by grasping the housing of the dropper 3, or even with the sample tube 5 mounted on the dropper 3, which is to be explained symbolically by the double arrow 13. In the last case shown in the drawings, a stable, positive connection which is advantageously rigid occurs between the dropper 3 and the sample tube 5 because the dropper 3 mounted or pushed on the attachment 6 is supported by the said attachment 6, and this facilitates spreading of the drop of fluid 1. Alternatively, it is possible to support the dropper 3 directly on the wall of the sample tube 5 or even directly on a cap, which does not have to be a screw cap, of the sample tube 5; in that case the membrane or seal 7 is accordingly an integral component of the sample tube or the cap.

Nevertheless, it is always achieved that only one part of the device comes into contact with the drop of fluid 1, that part being the dropper 3 integral with the spreader means 10. This means that only one part of the apparatus or device has to be discarded and becomes hazardous waste, i.e. only the dropper 3 which is also to be used as the spreader.

We claim:

1. A method of providing and spreading a drop of fluid on a slide, comprising:

pressing an end of a needle of a dropper through a seal into a container of fluid, the needle having a longitudinal channel to allow fluid to move from the container to an outlet of the dropper, the dropper including a spreader mounted thereon distal from the end of the needle and between the end of the needle and the outlet, the spreader having a linear edge;

applying a drop of fluid to a slide by using the dropper; and using the spreader to spread and distribute the drop of fluid on the slide.

2. The method of claim 1, wherein the spreader and the needle are integral parts of a body forming the dropper.

3. The method of claim 1, wherein the spreader extends radially with respect to the needle.

4. The method of claim 1, wherein the spreader extends transversely to the needle and projects on opposite sides of the needle.

5. A device for providing and spreading a drop of fluid on a slide, comprising a dropper including a needle having an end adapted to be pressed through a seal into a container of fluid, the needle having a longitudinal channel communicating between an inlet in the end of the needle and an outlet of the dropper, the dropper including a spreader mounted thereon distal from the end of the needle and between the end of the needle and the outlet, the spreader having a linear edge.

6. The device of claim 5, wherein the spreader is fixed to the needle.

7. The device of claim 6, wherein the spreader and the needle are integral parts of a body forming the dropper.

8. The device of claim 5, wherein the spreader extends radially with respect to the needle.

9. The device of claim 5, wherein the spreader extends transversely to the needle and projects on opposite sides of the needle.

10. A device for providing and spreading a drop of fluid on a slide, comprising a dropper including a needle having an end adapted to be pressed through a seal into a container of fluid, the needle having a longitudinal channel communicating between an inlet in the end of the needle and an outlet of the dropper, the dropper including a means for spreading mounted thereon distal from the end of the needle and between the end of the needle and the outlet, the spreading means having a linear edge.

11. The device of claim 10, wherein the means for spreading is fixed to the needle.

12. The device of claim 11, wherein the means for spreading and the needle are integral parts of a body forming the dropper.

13. The device of claim 10, wherein the means for spreading extends radially with respect to the needle.

14. The device of claim 10, wherein the means for spreading extends transversely to the needle and projects on opposite sides of the needle.

15. A device for providing and spreading a drop of fluid on a slide, comprising:

a fluid container having a seal; and a dropper adapted to be carried by the container, the dropper including a needle having an end which can be pressed through the seal into the fluid container, the needle having a longitudinal channel communicating between an inlet in the end of the needle and an outlet of the dropper, the dropper including a spreader mounted thereon distal from the end of the needle and between the end of the needle and the outlet, the spreader having a linear edge.

16. The device of claim 15, wherein the spreader is fixed to the needle.

17. The device of claim 16, wherein the spreader and the needle are integral parts of a body forming the dropper.

18. The device of claim 15, wherein the spreader extends radially with respect to the needle.

19. The device of claim 15, wherein the spreader extends transversely to the needle and projects on opposite sides of the needle.

* * * * *